(12) United States Patent
Ritter et al.

(10) Patent No.: US 11,514,623 B2
(45) Date of Patent: Nov. 29, 2022

(54) PROVIDING A MEDICAL IMAGE

(71) Applicants: Siemens Healthcare GmbH, Erlangen (DE); Universitat Zurich, Zurich (CH)

(72) Inventors: André Ritter, Neunkirchen am Brand (DE); Christian Hofmann, Erlangen (DE); Matthias Guckenberger, Maennedorf (CH); Stephanie Tanadini-Lang, Wettswil (CH)

(73) Assignees: UNVERSITÄT ZÜRICH, Zurich (CH); SIEMENS HEALTHCARE GMBH, Erlangen (DE)

( * ) Notice: Subject to any disclaimer, the term of this patent is extended or adjusted under 35 U.S.C. 154(b) by 933 days.

(21) Appl. No.: 16/253,269

(22) Filed: Jan. 22, 2019

(65) Prior Publication Data

US 2019/0236818 A1 Aug. 1, 2019

(30) Foreign Application Priority Data

Jan. 29, 2018 (EP) ...................... 8153904

(51) Int. Cl.
*G06T 11/00* (2006.01)
*A61B 6/03* (2006.01)
(Continued)

(52) U.S. Cl.
CPC ............ *G06T 11/008* (2013.01); *A61B 6/032* (2013.01); *A61B 6/481* (2013.01); *A61B 6/482* (2013.01);
(Continued)

(58) Field of Classification Search
CPC .... G16T 11/008; G16T 11/003; G16T 11/005; G06T 7/337; G06T 7/344; G06T 7/30;
(Continued)

(56) References Cited

U.S. PATENT DOCUMENTS 4,870,692 A * 9/1989 Zuiderveld ........... G06T 3/4007
382/107
2004/0081269 A1 4/2004 Pan et al.
(Continued)

FOREIGN PATENT DOCUMENTS

EP 1542165 A1 6/2005
EP 2037413 A2 3/2009

OTHER PUBLICATIONS

European Office Action for European Application No. EP 18153904 dated Jul. 23, 2018.

*Primary Examiner* — Peter Luong
(74) *Attorney, Agent, or Firm* — Harness, Dickey & Pierce, P.L.C.

(57) ABSTRACT

A method is for providing a medical image of a patient, acquired via a computed tomography apparatus. An embodiment of the method includes acquiring first projection data of a first measurement region; acquiring second projection data of a second measurement region; registering a reference image to the at least one respiration-correlated image of the patient, wherein the reference image corresponds to the at least one functional image of the patient or is reconstructed under a second reconstruction rule from the second projection data, to produce a deformation model; applying the deformation model to the at least one functional image of the patient; combining the at least one functional image of the patient, deformed by the applying of the deformation model, with the at least one respiration-correlated image of the patient, to produce the medical image of the patient; and providing the medical image of the patient.

19 Claims, 3 Drawing Sheets

(51) Int. Cl.
  *A61B 6/00* (2006.01)
  *G06T 7/33* (2017.01)
  *A61B 6/04* (2006.01)

(52) U.S. Cl.
  CPC .......... *A61B 6/5235* (2013.01); *A61B 6/5241* (2013.01); *A61B 6/5264* (2013.01); *G06T 7/337* (2017.01); *G06T 7/344* (2017.01); *A61B 6/0492* (2013.01); *A61B 6/504* (2013.01); *A61B 6/527* (2013.01); *A61B 6/5288* (2013.01); *G06T 2207/10081* (2013.01); *G06T 2207/20124* (2013.01); *G06T 2207/20224* (2013.01); *G06T 2207/30004* (2013.01); *G06T 2211/408* (2013.01)

(58) Field of Classification Search
  CPC . G06T 2207/10081; G06T 2207/20124; G06T 2207/20224; G06T 2207/30004; G06T 2211/408; G16H 30/20; A61B 6/032; A61B 6/481; A61B 6/482; A61B 6/5235; A61B 6/5241; A61B 6/5264; A61B 6/0492; A61B 6/504; A61B 6/527; A61B 6/5288

See application file for complete search history.

(56) References Cited

U.S. PATENT DOCUMENTS

| | | | |
|---|---|---|---|
| 2005/0053196 A1* | 3/2005 | Mostafavi | A61B 6/469 378/98.12 |
| 2007/0270689 A1 | 11/2007 | Lothert | |
| 2013/0060132 A1* | 3/2013 | Liao | G06T 7/0016 600/431 |

* cited by examiner

PROVIDING A MEDICAL IMAGE

PRIORITY STATEMENT

The present application hereby claims priority under 35 U.S.C. § 119 to European patent application number EP 18153904.0 filed Jan. 29, 2018, the entire contents of which are hereby incorporated herein by reference.

FIELD

Embodiments of the invention generally relate to a method for providing a medical image of a patient, which image has been acquired via a computed tomography apparatus, to a computed tomography system for providing a medical image of a patient, and to a computer program product.

BACKGROUND

In medical imaging, an imaging measurement sequence, which typically can be performed in a medical imaging modality, in particular in a computed tomography apparatus, is preferably optimized such that primarily a physiological state of a patient can be visible in a medical image. Various technical challenges mean that usually it is not possible, or only possible at high cost, to visualize in the medical image a plurality of, in particular different, physiological states of the patient, especially if the medical image has a relatively large measurement region, or if a plurality of medical images, which are meant to comprise each of the physiological states, are distributed over the measurement region.

SUMMARY

The inventors have discovered that problem can arise from the fact that first physiological states, in particular corresponding to breathing of the patient, and second physiological states, in particular corresponding to contrast enhancement in the patient and/or corresponding to an iodine distribution in the patient, differ in terms of their associated dynamic behavior. The different dynamic behavior means in particular that the imaging measurement sequence can typically be optimized with regard to acquiring the first physiological states or with regard to acquiring the second physiological states. In addition, a maximum field of view of the medical imaging modality is usually smaller than the measurement region associated with the imaging measurement sequence and needed for simultaneous acquisition of the first physiological states and the second physiological states. In other words, projection data comprising the first physiological states and the second physiological states can typically be acquired in succession, in particular cannot be acquired simultaneously.

At least one embodiment of the invention is directed to a method for providing a medical image of a patient, which image has been acquired via a computed tomography apparatus, a computed tomography system for providing a medical image of a patient, and a computer program product, wherein the medical image can comprise different physiological states or combinations of states.

Advantageous embodiments are described in the claims.

The method according to at least one embodiment of the invention for providing a medical image of a patient, acquired via a computed tomography apparatus, comprising:

acquiring first projection data of a first measurement region via the computed tomography apparatus, wherein at least one respiration-correlated image of the patient corresponding to respiration of the patient is reconstructed from the first projection data;

acquiring second projection data of a second measurement region via the computed tomography apparatus, wherein at least one functional image of the patient is reconstructed under a first reconstruction rule from the second projection data, and wherein the first measurement region and the second measurement region overlap at least partially;

registering a reference image to the at least one respiration-correlated image of the patient, wherein the reference image corresponds to the at least one functional image of the patient or is reconstructed under a second reconstruction rule from the second projection data, to produce a deformation model;

applying the deformation model to the at least one functional image of the patient;

combining the at least one functional image of the patient, deformed by the applying of the deformation model, with the at least one respiration-correlated image of the patient, to produce the medical image of the patient; and providing the medical image of the patient.

The computed tomography system according to at least one embodiment of the invention for providing a medical image of a patient comprises the computed tomography apparatus and a processing unit (including, for example, at least one processor), wherein the computed tomography apparatus comprises at least one X-ray source and at least one X-ray detector.

A computed tomography system according to at least one embodiment of the invention for providing a medical image of a patient, comprises:

a computed tomography apparatus, wherein the computed tomography apparatus comprises at least one X-ray source and at least one X-ray detector; and at least one processing unit, at least one of the computed tomography apparatus and the at least one processing unit being designed to perform at least:

acquiring first projection data of a first measurement region via the computed tomography apparatus, wherein at least one respiration-correlated image of the patient corresponding to respiration of the patient is reconstructed from the first projection data, acquiring second projection data of a second measurement region via the computed tomography apparatus, wherein at least one functional image of the patient is reconstructed under a first reconstruction rule from the second projection data, and wherein the first measurement region and the second measurement region overlap at least partially, registering a reference image to the at least one respiration-correlated image of the patient, wherein the reference image corresponds to the at least one functional image of the patient or is reconstructed under a second reconstruction rule from the second projection data, to produce a deformation model, applying the deformation model to the at least one functional image of the patient;

combining the at least one functional image of the patient, deformed by the applying of the deformation model, with the at least one respiration-correlated image of the patient, to produce the medical image of the patient, and providing the medical image of the patient.

The computer program product may comprise a computer program. The computer program product comprises in particular the program code segments/modules that models the method steps according to at least one embodiment of the invention. It is thereby possible to define and repeatedly perform the method according to at least one embodiment of the invention and to exercise control over disseminating the method according to at least one embodiment of the invention.

The computer program product is preferably configured such that the processing unit can use the computer program product to perform the method steps according to at least one embodiment of the invention. The program code segments/modules can be loaded, in particular, into a memory of the processing unit, and typically can be executed by a processor of the processing unit with access to the memory. When the computer program product, in particular the program code segments/modules, is executed in the processing unit, typically all the embodiments according to the invention of the described method can be implemented.

The computer program product is stored, for example, on a physical, computer-readable medium and/or digitally as a data packet in a computer network. The computer program product can constitute the physical, computer-readable medium and/or the data packet in the computer network. Hence the at least one embodiment of invention can also proceed from the physical computer-readable medium and/or from the data packet in the computer network. The physical, computer-readable medium can usually be connected directly to the processing unit, for instance by inserting the physical, computer-readable medium into a DVD drive or by plugging same into a USB port, whereby the processing unit can have access, in particular read access, to the physical, computer-readable medium. The data packet can preferably be retrieved from the computer network. The computer network can comprise the processing unit or be connected directly to the processing unit via a wide area network (WAN) connection and/or via a (wireless) local area network (WLAN or LAN) connection. For instance, the computer program product may be held digitally on a Cloud server at a storage location of the computer network, and be transferred via the WAN via the Internet and/or via the WLAN or LAN to the processing unit, in particular by opening a download link that points to the storage location of the computer program product.

BRIEF DESCRIPTION OF THE DRAWINGS

The invention is described and explained in greater detail below with reference to the example embodiments shown in the figures, where the same reference signs are used in the following description of the figures to denote structures and units that remain substantially the same as in the first appearance of the structure or unit concerned. In the drawings.

DETAILED DESCRIPTION OF THE EXAMPLE EMBODIMENTS

Figure 1:
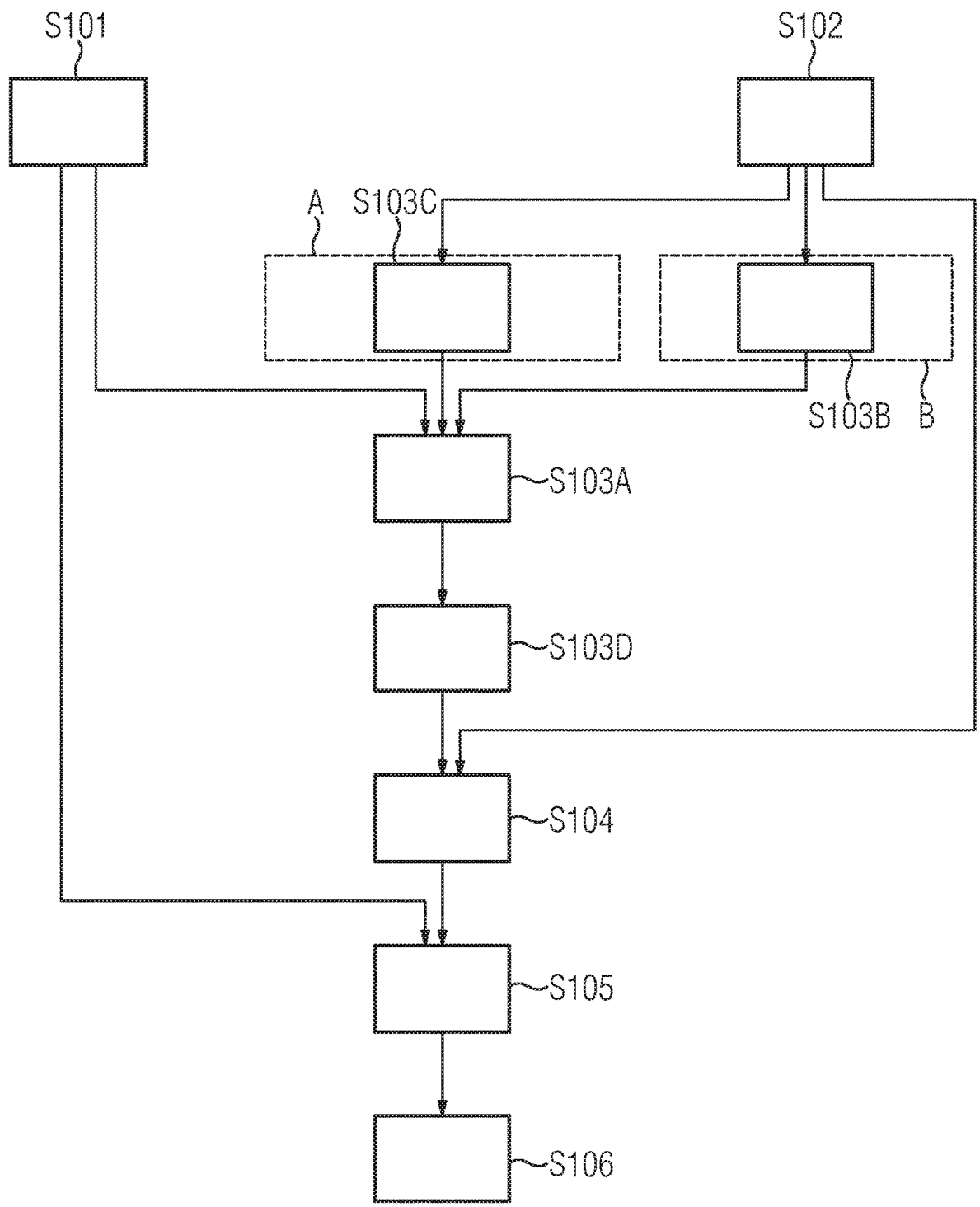
FIG. 1 shows a flow diagram of a method for providing a medical image of a patient, which image has been acquired via a computed tomography apparatus, in a first example embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

The method according to at least one embodiment of the invention for providing a medical image of a patient, acquired via a computed tomography apparatus, comprising:

acquiring first projection data of a first measurement region via the computed tomography apparatus, wherein at least one respiration-correlated image of the patient corresponding to respiration of the patient is reconstructed from the first projection data;

acquiring second projection data of a second measurement region via the computed tomography apparatus, wherein at least one functional image of the patient is reconstructed under a first reconstruction rule from the second projection data, and wherein the first measurement region and the second measurement region overlap at least partially;

registering a reference image to the at least one respiration-correlated image of the patient, wherein the reference image corresponds to the at least one functional image of the patient or is reconstructed under a second reconstruction rule from the second projection data, to produce a deformation model;

applying the deformation model to the at least one functional image of the patient;

combining the at least one functional image of the patient, deformed, with the at least one respiration-correlated image of the patient, to produce the medical image of the patient; and providing the medical image of the patient.

The acquisition of the first projection data and/or the second projection data can comprise performing an imaging measurement sequence in a medical imaging modality, in particular in the computed tomography apparatus. During the imaging measurement sequence, the patient is typically supported in the medical imaging modality, for instance on a patient couch, and/or positioned for the medical imaging modality. The first projection data and/or the second projection data can preferably be acquired via the computed tomography apparatus. The first measurement region is preferably modeled and/or described by the first projection data, in particular in performing a first imaging measurement sequence. The second measurement region is preferably modeled and/or described by the second projection data, in particular in performing a second imaging measurement sequence. The first imaging measurement sequence is typically performed before the second imaging measurement sequence. In principle, the second imaging measurement sequence can be performed before the first imaging measurement sequence.

The first projection data and/or the second projection data can comprise, for example, raw data from the computed tomography apparatus. The at least one respiration-correlated image and/or the at least one functional image of the patient are typically reconstructed from the first projection data and from the second projection data respectively using an iterative reconstruction technique and/or using filtered backprojection. The at least one respiration-correlated image of the patient and/or the at least one functional image of the patient preferably each comprise a distribution of image values, in particular a Hounsfield Unit distribution (HU).

The respiration of the patient can be determined by a physiological sensor system, for example, in particular during the first imaging measurement sequence. The physiological sensor system can comprise, for example, a breathing belt and/or a camera. For instance, the breathing belt or the camera can be used to determine a plurality of respiratory states of the respiration of the patient. An association of the plurality of respiratory states is preferably made to the first projection data and/or to the at least one respiration-correlated image. The plurality of respiratory states are typically cyclic and/or comprise, for example, the states of inhalation, mid-ventilation and/or exhalation. Alternatively or additionally, the respiration of the patient can be determined from the at least one respiration-correlated image, in particular via an image recognition algorithm. The at least one respiration-correlated image preferably comprises the respiration, in particular the plurality of respiratory states of the respiration, of the patient.

The at least one functional image comprises, for example, a plurality of states of the functional process, in particular of a contrast enhancement typically after injection of a contrast agent bolus, in the patient. The plurality of contrast-agent states usually become visible by the injection of the contrast agent bolus into the patient. The plurality of contrast-agent states comprise, for example, the states of no contrast enhancement, increasing contrast enhancement, maximum contrast enhancement and/or decreasing contrast enhancement. Alternatively or additionally, the at least one functional image can be reconstructed from the second projection data in such a way that the at least one functional image comprises a mixed image, a mono-energy image, a virtual non-contrast image, an image containing a fat distribution, an image containing an iodine distribution and/or an image containing an iron distribution. The image containing the iodine distribution may comprise, for instance, the contrast enhancement.

The first projection data and/or the second projection data can typically be divided into measurement data blocks. A measurement data block can comprise, for example, the projection data that has been acquired during a time interval. The time interval can typically correlate with a temporal resolution of the imaging measurement sequence or correspond to the temporal resolution of the imaging measurement sequence. Alternatively or additionally, the measurement data block can comprise the projection data that comprises and/or models a portion, in particular a spatial segment, of the first measurement region and/or of the second measurement region. For instance, the spatial segment can comprise a z-position of the first measurement region and/or of the second measurement region, and/or an extent of the first measurement region and/or of the second measurement region along the longitudinal axis of the patient couch. The patient couch is typically parallel to the z-axis of the medical imaging modality. The measurement data blocks can each comprise a state, in particular of the respiration and/or of the contrast enhancement.

The first measurement region and the second measurement region are preferably congruent. The first measurement region and/or the second measurement region are typically larger than a maximum field of view of the medical imaging modality, in particular than a maximum field of view of the computed tomography apparatus. An overlap between the first measurement region and the second measurement region, in particular parallel to the longitudinal axis of the patient couch, preferably equals more than 50%, particularly preferably more than 90%. The overlap between the first measurement region and the second measurement region can be referred to as a common measurement region, for example. The first measurement region and/or the second measurement region can comprise an organ of the patient, for instance a liver and/or a lung and/or a heart of the patient.

The first imaging measurement sequence and the second imaging measurement sequence can advantageously comprise different measurement parameters. For instance, a table speed of the second imaging measurement sequence is faster than a table speed of the first imaging measurement sequence, in particular faster by a factor of 1.5 or 2, particularly advantageously by a factor of 5. Preferably, the measurement parameters of the first imaging measurement sequence are optimized with regard to a time-resolved volumetric acquisition of the first projection data, and/or the measurement parameters of the second imaging measurement sequence are optimized with regard to the acquisition of the injection of the contrast agent bolus. The first imaging measurement sequence is preferably designed such that the first projection data comprises the respiration of the patient in particular at each z-position of the first measurement region. The first projection data advantageously comprises the same respiratory states at every z-position of the first measurement region. The first projection data is typically acquired until the first projection data has an identical number of respiratory states, in particular the same respiratory states, at every z-position of the first measurement region. In this case, the first measurement sequence can describe a spiral CT measurement sequence and/or a sequential CT measurement sequence.

The reconstruction rule comprises in particular a weighting of the projection data, in particular of the second projection data. For example, a contrast of the reconstructed image, in particular of the at least one functional image and/or of the reference image, varies according to the weighting of the projection data. The contrast typically depends on the distribution of image values. Different images and/or different distributions of image values, in particular with regard to the contrast, can preferably be reconstructed under the first reconstruction rule and under the second reconstruction rule respectively.

The deformation field can comprise in particular a vector field, which models a change between two registration images, in particular between a start image and a target image. For instance, the two registration images comprise the at least one respiration-correlated image and the reference image. The deformation field can comprise a plurality of vector fields, which describe a path from the start image to the target image. By applying the deformation field, the projection data, in particular the at least one respiration-correlated image and/or the reference image, are deformed such that the start image preferably equates to the target image, in particular with regard to contours. The contours can delineate, for example, the organ and/or tissue and/or vessels and/or bone material and/or a tumor. The deformation can preferably be inverted by inverting the deformation field. The at least one respiration-correlated image and the reference image are typically the start image and the target image respectively, or vice versa. In other words, depending on the implementation, the deformation field typically can be produced starting from the at least one respiration-correlated image or starting from the at least one functional image, and applied accordingly.

If the reference image corresponds to the at least one functional image of the patient, the at least one functional image in particular is used for the registration. In this case, the at least one functional image is typically the start image or the target image.

If the reference image is reconstructed under a second reconstruction rule from the second projection data, an image that is different from the at least one functional image in particular is reconstructed from the second projection data. The second reconstruction rule typically differs from the first reconstruction rule in the manner that different images, in particular functional images, are reconstructed when each reconstruction rule is applied to the second projection data. The second reconstruction rule is preferably optimized such that the registration of the reference image based on the second reconstruction rule delivers better results, in particular a more exact deformation model, than the registration of the reference image based on the first reconstruction rule.

In principle, the registration can comprise minimizing an image-value based difference measure. The image-value based difference measure can represent, for example, a sum or a mean value of the squared differences, which squared differences are formed at points, between the reference image, in particular the distribution of image values in the reference image, and the at least one respiration-correlated image, in particular the distribution of image values in the respiration-correlated image, of the patient. The image-value based difference measure may be unsuitable, for instance because of a systemic change in the patient, for example in the contrast enhancement. In this case, a local cross-correlation difference measure and/or a mutual-information difference measure can be used, for example.

Applying the deformation model comprises in particular deforming the at least one functional image in such a way that contours of the at least one functional image equate to the contours of the at least one respiration-correlated image. If the reference image is reconstructed under a second reconstruction rule from the second projection data, advantageously the deformation model is determined for first registration images, and the deformation model applied for second registration images, wherein the first registration images and the second registration images each typically have in common only a single image, in particular the target image, i.e. typically the at least one respiration-correlated image.

Combining preferably comprises comparing arithmetically the deformed at least one functional image of the patient against the at least one respiration-correlated image of the patient in such a way that the medical image for instance intensifies and/or distinguishes image information in the deformed at least one functional image and image information in the at least one respiration-correlated image. In this case, the medical image typically emerges as a single image from combining the at least one functional image and the at least one respiration-correlated image. Alternatively or additionally, combining can be performed in such a way that the medical image comprises a medical image dataset, wherein the medical image dataset comprises the at least one functional image and the at least one respiration-correlated image. In other words, the at least one functional image and the at least one respiration-correlated image are contained in a single medical image dataset, albeit typically as separate images. It is conceivable that the medical image dataset comprises the separate images and a combined medical image.

Providing the medical image can comprise transferring the medical image from the computed tomography apparatus into a radiology information system and/or a PACS picture archiving system. Alternatively or additionally, the medical image can be displayed on a monitor, in particular to the user. The monitor is preferably designed, for example, to retrieve the medical image from the radiology information system and/or the PACS picture archiving system, and/or from the medical imaging modality, and/or to display the medical image. In principle it is conceivable that the medical image can be exchanged via a network that connects, for instance, the radiology information system and/or the PACS picture archiving system and/or the medical imaging modality, and can be stored and/or retrieved on a server, for example. In addition to the medical image, the first projection data and/or the second projection data, for example, can be provided, in particular can be transferred into the radiology information system and/or the PACS picture archiving system and/or displayed on the monitor.

The method according to at least one embodiment of the invention for providing the medical image of the patient in particular brings the following advantages:

Producing the medical image, which preferably comprises the image information from images reconstructed on the basis of two separately performed imaging measurement sequences, is in particular advantageous for a user, in particular a doctor, when the doctor is carrying out, for example, radiation treatment planning for cancer treatment of the patient. In particular if the radiation treatment planning relates to an organ that, as a result of the positioning, may move relative to the thorax of the patient because of breathing or beating of the heart, the medical image can facilitate on the basis of the at least one respiration-correlated image, an assessment of the movement of the organ, and, on the basis of the at least one functional image, an assessment of the functional process, in particular necrosis and/or perfusion and/or capillarization inside the organ. Typically, the medical image can advantageously comprise the iodine distribution in the patient for the inhalation respiratory state and/or, for example, the iodine distribution in the patient for the exhalation respiratory state.

Producing the medical image is also advantageous in terms of reducing a length of examination of the patient. The length of examination of the patient when performing the imaging measurement sequence in the computed tomography apparatus is typically correlated with X-rays that are potentially harmful to the patient, in particular correlated with an X-ray dose. The length of examination and/or preferably the X-ray dose corresponding to the X-ray radiation can be reduced by combining the first projection data, in particular the at least one respiration-correlated image, and the second projection data, in particular the at least one functional image.

If the reference image is reconstructed under the second reconstruction rule from the second projection data, it is preferably possible to reconstruct on the basis of the second projection data under the second reconstruction rule an image that is optimum with regard to the registration, and to apply the deformation model produced therefrom to the at least one functional image, for example.

According to one embodiment, the deformed at least one functional image of the patient is combined with the at least one respiration-correlated image of the patient in such a way that the medical image of the patient comprises a subtraction image of the patient, which image comprises the contrast enhancement of the patient. The subtraction image preferably comprises solely the contrast enhancement of the patient. In other words, the subtraction eliminates from the medical image in particular tissue or bone material not enhanced by contrast agent. In principle it is conceivable that the subtraction image comprises the image of the iodine distribution, the image of the fat distribution and/or the image of the iron distribution. For example, the deformed at least one functional image of the patient and the at least one respiration-correlated image of the patient are compared arithmetically in such a way that the at least one respiration-correlated image of the patient is subtracted from the deformed at least one functional image of the patient. The difference typically represents the contrast enhancement in the patient before and after injection of the contrast agent bolus. The subtraction image is produced in particular by combining a pre-contrast image and a post-contrast image, wherein typically the pre-contrast image comprises image information before the contrast enhancement, and the post-contrast image comprises image information after the contrast enhancement in the particular measurement region.

According to one embodiment, the contrast agent bolus is injected into the patient after the acquisition of the first projection data and before the acquisition of the second projection data. In this case, the pre-contrast image can be reconstructed not from the second projection data but typically solely from the first projection data. Preferably, the pre-contrast image is reconstructed from the first projection data, and the post-contrast image from the second projection data. This is advantageous in particular because acquiring the second projection data can turn out to be shorter, whereby in particular the X-ray dose for the patient can be reduced. This embodiment is therefore confined in particular to digital subtraction angiography. The pre-contrast image and the post-contrast image are advantageously reconstructed from different projection data, whereby the first imaging measurement sequence and the second imaging measurement sequence can be parameterized independently of one another and/or can be optimized, in particular with regard to the X-ray dose. In contrast, digital subtraction angiography usually requires that the pre-contrast image and the post-contrast image are reconstructed from the same projection data.

According to one embodiment, the second projection data and the reference image reconstructed therefrom comprise the plurality of states of the contrast enhancement in the patient, and the reference image is registered to the at least one respiration-correlated image of the patient on the basis of the plurality of states of the contrast enhancement. If the reference image is registered to the at least one respiration-correlated image of the patient on the basis of the plurality of states of the contrast enhancement, the reference image is preferably registered in accordance with a ranking of the states of the contrast enhancement. In other words, the reference image that preferably is comparatively most similar to the at least one respiration-correlated image, is preferably registered first to the at least one respiration-correlated image, and so on. On the basis of the plurality of states of the contrast enhancement means in particular that, for example, the second projection data is sorted such that the contrast enhancement is increasing or decreasing. Other rankings are also conceivable. The deformation model, in particular the vector fields, can preferably be produced and/or applied to the at least one functional image progressively in accordance with the increase in the contrast enhancement.

According to one embodiment, the at least one respiration-correlated image for a plurality of respiratory states of the respiration of the patient is reconstructed from the first projection data, and a plurality of deformation models are produced by registering the reference image to the corresponding at least one respiration-correlated image for the plurality of respiratory states of the respiration of the patient. In other words, the plurality of deformation models can preferably be produced on the basis of the plurality of respiratory states.

According to one embodiment, the medical image for the plurality of respiratory states of the respiration of the patient is produced by applying the plurality of deformation models to the at least one functional image of the patient and by combining the deformed at least one functional image for the plurality of respiratory states of the patient with the at least one respiration-correlated image of the patient. The at least one respiration-correlated image for a plurality of respiratory states of the respiration of the patient therefore comprises, for example, image information during inhalation and image information during exhalation. In this case, the plurality of deformation models allow the at least one functional image to be deformed such that in particular the contours of the deformed at least one functional image of the patient are adapted to the inhalation or to the exhalation respectively. The medical image for the plurality of respiratory states of the respiration of the patient advantageously comprises the deformed at least one functional image, for instance during inhalation and/or during exhalation.

According to one embodiment, the second projection data is acquired via an imaging spectral measurement sequence in the computed tomography apparatus, and comprises a first energy band and a second energy band. In this case, in particular the second imaging measurement sequence corresponds to the imaging spectral measurement sequence. The first energy band and the second energy band differ, for example, in terms of an energy of the X-rays. The image information of the at least one respiration-correlated image and/or the image information of the at least one functional image usually depends on the first energy band and/or the second energy band. For instance, an X-ray source produces the X-rays distributed over an X-ray spectrum as a function of the applied acceleration voltage between cathode and anode. The first energy band and the second energy band may differ in terms of the acceleration voltage, for instance. It is usually possible to vary over time the acceleration voltage within the same X-ray source, and/or to use two X-ray sources, in which case typically both X-ray sources are operated using different acceleration voltages. A computed tomography apparatus comprising two X-ray sources is typically called a dual-source and/or dual-energy computed tomography apparatus. Both X-ray sources can preferably emit the X-rays simultaneously, in particular in accordance with the second imaging measurement sequence. Alternatively or additionally, the X-rays are detected by an energy-sensitive X-ray detector, for instance a photon-counting detector. If the second projection data comprises the first energy band and the second energy band, it is advantageously possible to reconstruct from the second projection data the mixed image, in particular for 120 keV, the mono-energy image, the virtual non-contrast image, the image containing the fat distribution, the image containing the iodine distribution and/or the image containing the iron distribution.

According to one embodiment, the reference image is reconstructed under the second reconstruction rule from the second projection data, wherein the first reconstruction rule specifies a first mixing of the second projection data according to the first energy band and the second energy band, and wherein the second reconstruction rule specifies a second mixing of the second projection data according to the first energy band and the second energy band. The first mixing and/or the second mixing typically each specify combining the first projection data with the second projection data and/or applying a multiband filter to the first projection data and/or to the second projection data using different weightings. Particularly advantageously for this embodiment, the second projection data is acquired in a dual-source computed tomography apparatus and/or using the photon-counting detector. The reference image based on the second reconstruction rule, for instance the mixed image and/or the virtual non-contrast image, is typically more similar, in particular on an image-value basis, to the at least one respiration-correlated image than the at least one functional image based on the first reconstruction rule, in particular the image containing the fat distribution, the image containing the iodine distribution and/or the image containing the iron distribution.

According to one embodiment, the reference image is reconstructed under the second reconstruction rule from the second projection data, wherein the first reconstruction rule is optimized with regard to a functional contrast, and wherein the second reconstruction rule is optimized with regard to an anatomical contrast. In other words, the first reconstruction rule, in particular the first mixing, and the second reconstruction rule, in particular the second mixing, are designed such that preferably the reference image based on the second reconstruction rule and the at least one respiration-correlated image comprise an anatomy of the patient, while the at least one functional image based on the first reconstruction rule preferably comprises the functional process, for instance the contrast enhancement. The reference image advantageously comprises the optimized anatomical contrast, thereby typically improving the registration of the reference image to the at least one respiration-correlated image and hence the deformation model. In other words, an optimum deformation model can advantageously be calculated based solely on the second projection data, the optimum deformation model being applied advantageously to the at least one functional image, which in turn is based on the second projection data.

The computed tomography system according to at least one embodiment of the invention for providing a medical image of a patient comprises the computed tomography apparatus and a processing unit (including, for example, at least one processor), wherein the computed tomography apparatus comprises at least one X-ray source and at least one X-ray detector.

In at least one embodiment, the computed tomography apparatus is preferably designed to perform the first imaging measurement sequence and/or the second imaging measurement sequence. The processing unit can be connected, for instance via the network, to the radiology information system and/or the PACS picture archiving system for the purpose of providing the medical image. Alternatively or additionally, the computed tomography system for providing the medical image of the patient, in particular the processing unit, can comprise the monitor.

The processing unit is preferably connected to the computed tomography apparatus such that the first projection data, which is acquired in particular in performing the first imaging measurement sequence, and/or the second projection data, which is acquired in particular in performing the second imaging measurement sequence, can be transferred from the computed tomography apparatus to the processing unit.

According to one embodiment, the computed tomography apparatus comprises two X-ray sources and two X-ray detectors. In this case, the computed tomography apparatus may be called a dual-source computed tomography apparatus and/or a dual-energy computed tomography apparatus.

The computer program product according to at least one embodiment of the invention comprises program code segments/modules that can be loaded into the processing unit in order to perform a method according to at least one embodiment of the invention for providing a medical image of a patient when the program code segments/modules is executed in the processing unit.

The computer program product may comprise a computer program. The computer program product comprises in particular the program code segments/modules that models the method steps according to at least one embodiment of the invention. It is thereby possible to define and repeatedly perform the method according to at least one embodiment of the invention and to exercise control over disseminating the method according to at least one embodiment of the invention.

The computer program product is preferably configured such that the processing unit can use the computer program product to perform the method steps according to at least one embodiment of the invention. The program code segments/modules can be loaded, in particular, into a memory of the processing unit, and typically can be executed by a processor of the processing unit with access to the memory. When the computer program product, in particular the program code segments/modules, is executed in the processing unit, typically all the embodiments according to the invention of the described method can be implemented.

The computer program product is stored, for example, on a physical, computer-readable medium and/or digitally as a data packet in a computer network. The computer program product can constitute the physical, computer-readable medium and/or the data packet in the computer network. Hence the at least one embodiment of invention can also proceed from the physical computer-readable medium and/or from the data packet in the computer network. The physical, computer-readable medium can usually be connected directly to the processing unit, for instance by inserting the physical, computer-readable medium into a DVD drive or by plugging same into a USB port, whereby the processing unit can have access, in particular read access, to the physical, computer-readable medium. The data packet can preferably be retrieved from the computer network. The computer network can comprise the processing unit or be connected directly to the processing unit via a wide area network (WAN) connection and/or via a (wireless) local area network (WLAN or LAN) connection. For instance, the computer program product may be held digitally on a Cloud server at a storage location of the computer network, and be transferred via the WAN via the Internet and/or via the WLAN or LAN to the processing unit, in particular by opening a download link that points to the storage location of the computer program product.

FIG. 1 shows a flow diagram of a method for providing a medical image of a patient, which image has been acquired via a computed tomography apparatus, in a first example embodiment.

Method step S101 denotes acquiring first projection data of a first measurement region via the computed tomography apparatus, wherein at least one respiration-correlated image of the patient corresponding to respiration of the patient is reconstructed from the first projection data.

Method step S102 denotes acquiring second projection data of a second measurement region via the computed tomography apparatus, wherein at least one functional image of the patient is reconstructed under a first reconstruction rule from the second projection data, and wherein the first measurement region and the second measurement region overlap at least partially.

Method step S103A denotes registering a reference image to the at least one respiration-correlated image of the patient.

Method step S103B and method step S103C form two alternatives A and B. In other words, either method step S103B or method step S103C is performed. That is to say, method step S103B and method step S103C provide two independent options A, B for obtaining the reference image.

Method step S103B denotes that the reference image corresponds to the at least one functional image of the patient.

Method step S103C denotes that the reference image is reconstructed under a second reconstruction rule from the second projection data.

Method step S103D denotes that a deformation model is produced.

Method step S104 denotes applying the deformation model to the at least one functional image of the patient.

Method step S105 denotes combining the deformed at least one functional image of the patient with the at least one respiration-correlated image of the patient, thereby producing the medical image of the patient.

Method step S106 denotes providing the medical image of the patient.

Figure 2:
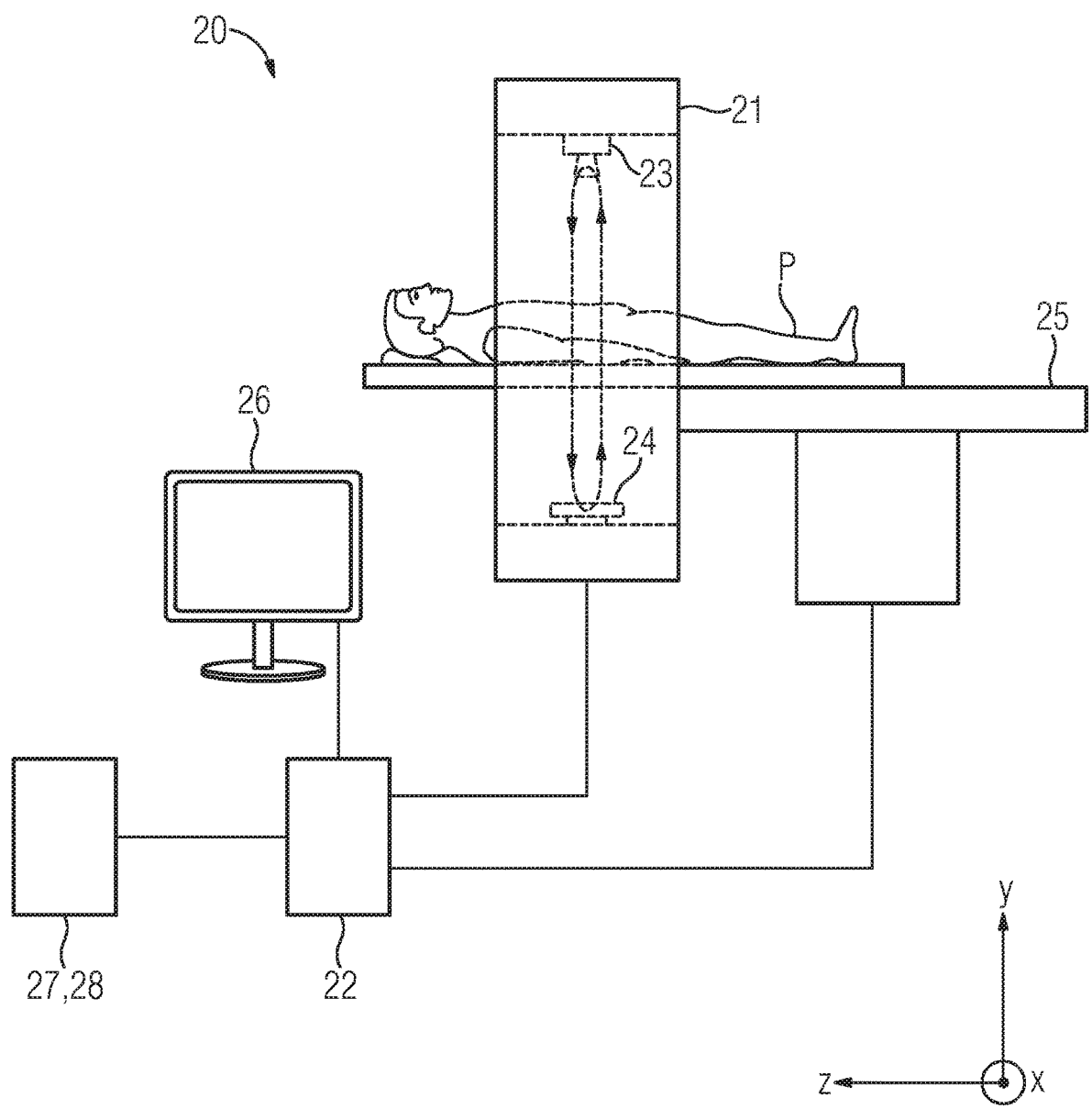
FIG. 2 shows a computed tomography system for providing a medical image of a patient.

FIG. 2 shows a computed tomography system 20 for providing a medical image of a patient P, which computed tomography system 20 comprises a computed tomography apparatus 21 and a processing unit 22. The computed tomography apparatus 21 comprises at least one X-ray source 23 and at least one X-ray detector 24, the at least one X-ray source 23 and the at least one X-ray detector 24 being arranged such that they can rotate about a patient couch 25. The patient P is supported on the patient couch 25, which patient couch 25 is designed to be parallel to the spatial axis z. The processing unit 22 comprises a monitor 26, which comprises, for example, a graphical user interface and input device(s). For instance, the user and/or the doctor can use the graphical user interface to specify measurement parameters of a first imaging measurement sequence and/or of a second imaging measurement sequence. The processing unit 22 is connected to a radiology information system 27 and to a PACS picture archiving system 28.

In principle it is conceivable that the computed tomography apparatus 21 comprises two X-ray sources and two X-ray detectors, with preferably both X-ray sources having different acceleration voltages, in particular during the second imaging measurement sequence. In this case, the second projection data preferably comprises a first energy band and a second energy band.

Figure 3:
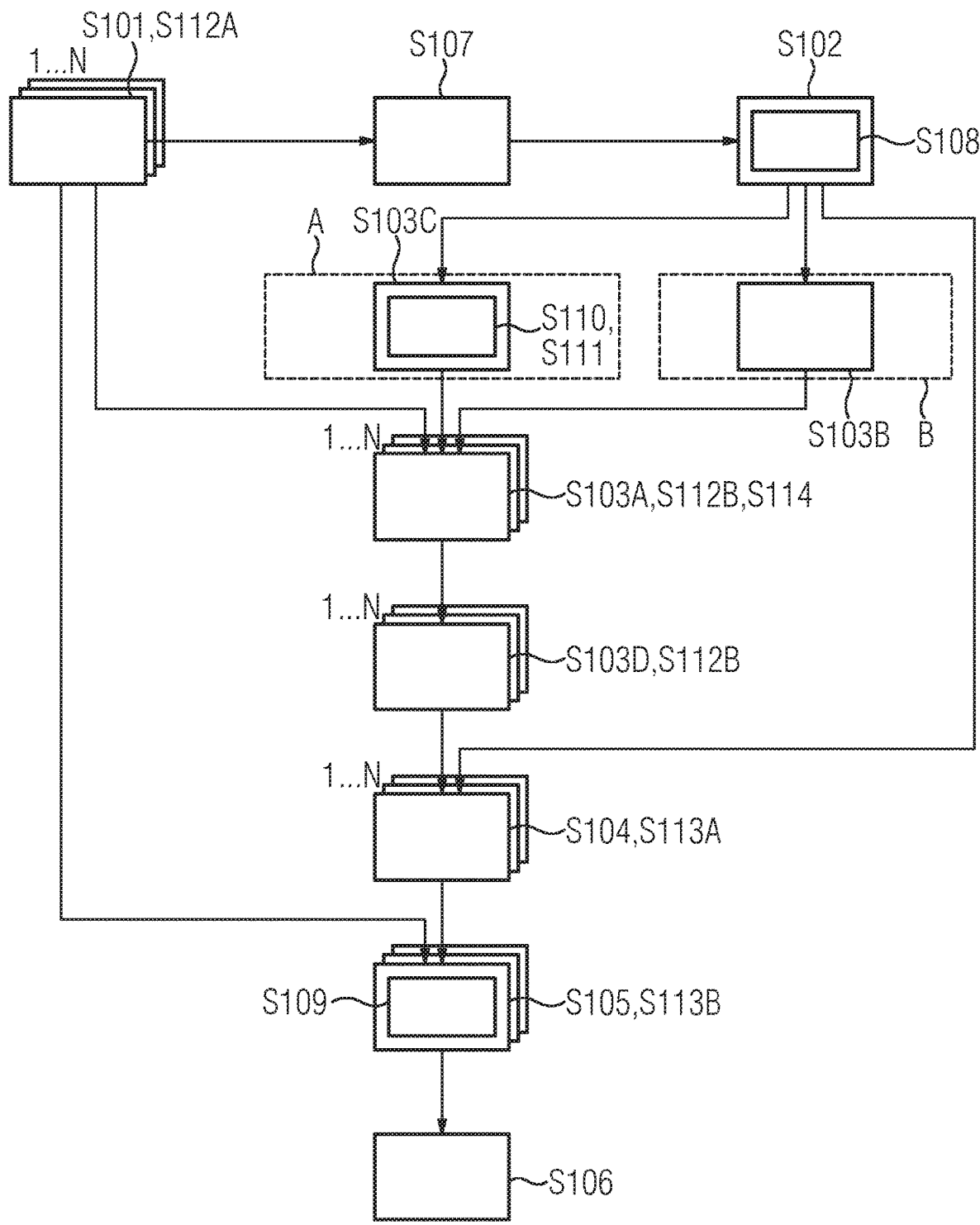
FIG. 3 shows a flow diagram of a method for providing a medical image of a patient, which image has been acquired via a computed tomography apparatus, in a second example embodiment.

FIG. 3 shows a flow diagram of a method for providing a medical image of a patient, which image has been acquired via a computed tomography apparatus, in a second example embodiment. The method steps S107 to S114 shown in FIG. 3 can be combined practically in any way.

Method step S107 denotes that a contrast agent bolus is injected into the patient after the acquisition of the first projection data and before the acquisition of the second projection data.

Method step S108 denotes that the second projection data is acquired via an imaging spectral measurement sequence in the computed tomography apparatus, and comprises a first energy band and a second energy band.

Method step S110 denotes that the reference image is reconstructed under the second reconstruction rule from the second projection data, wherein the first reconstruction rule specifies a first mixing of the second projection data according to the first energy band and the second energy band, and wherein the second reconstruction rule specifies a second mixing of the second projection data according to the first energy band and the second energy band.

Method step S111 denotes that the reference image is reconstructed under the second reconstruction rule from the second projection data, wherein the first reconstruction rule is optimized with regard to a functional contrast, and wherein the second reconstruction rule is optimized with regard to an anatomical contrast.

Method step S112A denotes that the at least one respiration-correlated image for a plurality of respiratory states of the respiration of the patient is reconstructed from the first projection data.

Method step S112B denotes that a plurality of deformation models are produced by registering the reference image to the corresponding at least one respiration-correlated image for the plurality of respiratory states of the respiration of the patient.

Method step S113A denotes that the plurality of deformation models are applied to the at least one functional image of the patient.

Method step S113B denotes that the medical image for the plurality of respiratory states of the respiration of the patient is produced by combining the deformed at least one functional image for the plurality of respiratory states of the patient with the at least one respiration-correlated image of the patient. The medical image may comprise a medical image dataset, the medical image dataset comprising separate images for the respective respiratory states of the respiration of the patient.

Method step S114 denotes that the second projection data and the reference image reconstructed therefrom comprise a plurality of states of a contrast enhancement in the patient, wherein the reference image is registered to the at least one respiration-correlated image of the patient on the basis of the plurality of states of the contrast enhancement.

Method step S109 denotes that the deformed at least one functional image of the patient is combined with the at least one respiration-correlated image of the patient in such a way that the medical image of the patient comprises a subtraction image of the patient, which image comprises the contrast enhancement of the patient.

Although the invention has been illustrated and described in detail using the preferred example embodiments, the invention is not limited by the disclosed examples, and a person skilled in the art can derive other variations therefrom that are still covered by the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing a medical image of a patient, acquired via a computed tomography apparatus, comprising:
    acquiring first projection data of a first measurement region via the computed tomography apparatus, wherein at least one respiration-correlated image of the patient corresponding to respiration of the patient is reconstructed from the first projection data;
    acquiring second projection data of a second measurement region via the computed tomography apparatus, wherein at least one functional image of the patient is reconstructed under a first reconstruction rule from the second projection data, and wherein the first measurement region and the second measurement region overlap at least partially;
    registering a reference image to the at least one respiration-correlated image of the patient, wherein the reference image corresponds to the at least one functional image of the patient or is reconstructed under a second reconstruction rule from the second projection data, to produce a deformation model;
    applying the deformation model to the at least one functional image of the patient;
    combining the at least one functional image of the patient, deformed by the applying of the deformation model, with the at least one respiration-correlated image of the patient, to produce the medical image of the patient; and
    providing the medical image of the patient.

2. The method of claim 1, wherein the at least one functional image of the patient, deformed by the applying of the deformation model, is combined with the at least one respiration-correlated image of the patient such that the medical image of the patient comprises a subtraction image of the patient, the subtraction image including a contrast enhancement of the patient.

3. The method of claim 2, further comprising:
    injecting a contrast agent bolus into the patient after the acquiring of the first projection data and before the acquiring of the second projection data.

4. The method of claim 2, wherein the second projection data and the reference image reconstructed from the second projection data comprise a plurality of states of a contrast enhancement in the patient, and wherein the reference image is registered to the at least one respiration-correlated image of the patient based upon the plurality of states of the contrast enhancement.

5. The method of claim 2, wherein the at least one respiration-correlated image for a plurality of respiratory states of respiration of the patient is reconstructed from the first projection data, and wherein a plurality of deformation models are produced by registering the reference image to the corresponding at least one respiration-correlated image for the plurality of respiratory states of the respiration of the patient.

6. The method of claim 5, wherein the medical image for the plurality of respiratory states of the respiration of the patient is produced by applying the plurality of deformation models to the at least one functional image of the patient and by combining the at least one functional image, deformed by the applying of the deformation model, for the plurality of respiratory states of the patient with the at least one respiration-correlated image of the patient.

7. The method of claim 2, wherein the second projection data is acquired via an imaging spectral measurement sequence in the computed tomography apparatus, and comprises a first energy band and a second energy band.

8. The method of claim 7, wherein the reference image is reconstructed under a second reconstruction rule from the second projection data, and wherein a first reconstruction rule specifies a first mixing of the second projection data according to the first energy band and the second energy band, and wherein the second reconstruction rule specifies a second mixing of the second projection data according to the first energy band and the second energy band.

9. The method of claim 8, wherein the reference image is reconstructed under the second reconstruction rule from the second projection data, wherein the first reconstruction rule is optimized with regard to a functional contrast, and wherein the second reconstruction rule is optimized with regard to an anatomical contrast.

10. The method of claim 1, further comprising:
injecting a contrast agent bolus into the patient after the acquiring of the first projection data and before the acquiring of the second projection data.

11. The method of claim 1, wherein the second projection data and the reference image reconstructed from the second projection data comprise a plurality of states of a contrast enhancement in the patient, and wherein the reference image is registered to the at least one respiration-correlated image of the patient based upon the plurality of states of the contrast enhancement.

12. The method of claim 1, wherein the at least one respiration-correlated image for a plurality of respiratory states of respiration of the patient is reconstructed from the first projection data, and wherein a plurality of deformation models are produced by registering the reference image to the corresponding at least one respiration-correlated image for the plurality of respiratory states of the respiration of the patient.

13. The method of claim 12, wherein the medical image for the plurality of respiratory states of the respiration of the patient is produced by applying the plurality of deformation models to the at least one functional image of the patient and by combining the at least one functional image, deformed by the applying of the deformation model, for the plurality of respiratory states of the patient with the at least one respiration-correlated image of the patient.

14. The method of claim 1, wherein the second projection data is acquired via an imaging spectral measurement sequence in the computed tomography apparatus, and comprises a first energy band and a second energy band.

15. The method of claim 14, wherein the reference image is reconstructed under a second reconstruction rule from the second projection data, and wherein a first reconstruction rule specifies a first mixing of the second projection data according to the first energy band and the second energy band, and wherein the second reconstruction rule specifies a second mixing of the second projection data according to the first energy band and the second energy band.

16. The method of claim 15, wherein the reference image is reconstructed under the second reconstruction rule from the second projection data, wherein the first reconstruction rule is optimized with regard to a functional contrast, and wherein the second reconstruction rule is optimized with regard to an anatomical contrast.

17. A computed tomography system for providing a medical image of a patient, comprising:
a computed tomography apparatus, wherein the computed tomography apparatus comprises at least one X-ray source and at least one X-ray detector; and
at least one processing unit, at least one of the computed tomography apparatus and the at least one processing unit being designed to perform at least:
acquiring first projection data of a first measurement region via the computed tomography apparatus, wherein at least one respiration-correlated image of the patient corresponding to respiration of the patient is reconstructed from the first projection data,
acquiring second projection data of a second measurement region via the computed tomography apparatus, wherein at least one functional image of the patient is reconstructed under a first reconstruction rule from the second projection data, and wherein the first measurement region and the second measurement region overlap at least partially,
registering a reference image to the at least one respiration-correlated image of the patient, wherein the reference image corresponds to the at least one functional image of the patient or is reconstructed under a second reconstruction rule from the second projection data, to produce a deformation model,
applying the deformation model to the at least one functional image of the patient;
combining the at least one functional image of the patient, deformed by the applying of the deformation model, with the at least one respiration-correlated image of the patient, to produce the medical image of the patient; and
providing the medical image of the patient.

18. A computed tomography system as claimed in claim 17, wherein the computed tomography apparatus comprises two X-ray sources and two X-ray detectors.

19. A non-transitory computer readable medium comprising program code segments, loadable into a processing unit, the program code segments configured to instruct a computed tomography apparatus to
acquire first projection data of a first measurement region via the computed tomography apparatus, wherein at least one respiration-correlated image of a patient corresponding to respiration of the patient is reconstructed from the first projection data;
acquire second projection data of a second measurement region via the computed tomography apparatus, wherein at least one functional image of the patient is reconstructed under a first reconstruction rule from the second projection data, and wherein the first measurement region and the second measurement region overlap at least partially;
register a reference image to the at least one respiration-correlated image of the patient, wherein the reference image corresponds to the at least one functional image of the patient or is reconstructed under a second reconstruction rule from the second projection data, to produce a deformation model;
apply the deformation model to the at least one functional image of the patient;

combine the at least one functional image of the patient, deformed by the applying of the deformation model, with the at least one respiration-correlated image of the patient, to produce a medical image of the patient; and provide the medical image of the patient.

\* \* \* \* \*

UNITED STATES PATENT AND TRADEMARK OFFICE
CERTIFICATE OF CORRECTION

| | |
|---|---|
| PATENT NO. | : 11,514,623 B2 |
| APPLICATION NO. | : 16/253269 |
| DATED | : November 29, 2022 |
| INVENTOR(S) | : Andre Ritter et al. |

It is certified that error appears in the above-identified patent and that said Letters Patent is hereby corrected as shown below:

On the Title Page

Item (30) should read:
(30) Foreign Application Priority Data
January 29, 2018 (EP).... 18153904.0

Signed and Sealed this
Seventh Day of March, 2023

Katherine Kelly Vidal
*Director of the United States Patent and Trademark Office*